US010125454B2

(12) United States Patent
Ladisch et al.

(10) Patent No.: US 10,125,454 B2
(45) Date of Patent: *Nov. 13, 2018

(54) FLOW PROCESS FOR PRETREATMENT OF LIGNOCELLULOSIC BIOMASS

(75) Inventors: Michael R. Ladisch, West Lafayette, IN (US); Brian Stater, Noblesville, IN (US); Bradley Spindler, Fishers, IN (US)

(73) Assignees: Purdue Research Foundation, West Lafayette, IN (US); Bowen Engineering Corporation, Indianapolis, IN (US)

( * ) Notice: Subject to any disclaimer, the term of this patent is extended or adjusted under 35 U.S.C. 154(b) by 480 days.

This patent is subject to a terminal disclaimer.

(21) Appl. No.: 13/001,130

(22) PCT Filed: Jun. 26, 2009

(86) PCT No.: PCT/US2009/048863
§ 371 (c)(1),
(2), (4) Date: Mar. 25, 2011

(87) PCT Pub. No.: WO2009/158621
PCT Pub. Date: Dec. 30, 2009

(65) Prior Publication Data
US 2011/0183379 A1    Jul. 28, 2011

Related U.S. Application Data

(60) Provisional application No. 61/076,019, filed on Jun. 26, 2008.

(51) Int. Cl.
| C12N 9/24 | (2006.01) |
| C12P 7/10 | (2006.01) |
| C12P 19/02 | (2006.01) |
| C12P 19/10 | (2006.01) |
| D21C 11/00 | (2006.01) |
| C12P 19/14 | (2006.01) |

(52) U.S. Cl.
CPC .......... D21C 11/0007 (2013.01); C12P 7/10 (2013.01); C12P 19/02 (2013.01); C12P 19/14 (2013.01); *C12P 2201/00* (2013.01); *Y02E 50/16* (2013.01)

(58) Field of Classification Search
None
See application file for complete search history.

(56) References Cited

U.S. PATENT DOCUMENTS

| 1,905,050 | A | | 4/1933 | Pelot et al. | |
| 4,340,446 | A | * | 7/1982 | Crawford | 203/19 |
| 5,411,594 | A | * | 5/1995 | Brelsford | B01J 19/242 127/1 |
| 5,497,824 | A | * | 3/1996 | Rouf | F28F 13/12 138/38 |
| 5,846,787 | A | * | 12/1998 | Ladisch | C12P 19/04 435/99 |
| 7,297,236 | B1 | * | 11/2007 | Vander Griend | B01D 3/005 202/153 |
| 9,777,341 | B2 | | 10/2017 | Ladisch et al. | |
| 2002/0148575 | A1 | * | 10/2002 | Wingerson | 162/14 |
| 2006/0286628 | A1 | * | 12/2006 | Everett | B01D 3/06 435/41 |
| 2008/0029233 | A1 | | 2/2008 | Wingerson | |
| 2008/0057541 | A1 | | 3/2008 | Hill et al. | |

OTHER PUBLICATIONS

Bartlett, D.A., "The Fundamentals of Heat Exchangers," The Industrial Physicist, The American Institute of Physics, pp. 18-21 (1996).*
Bartlett, D.A., "The Fundamentals of Heat Exchangers," The Industrial Physicist, The American Institute of Physics, pp. 18-21 (1996; of record).*
Master et al. (Engineering Conferences International Digital Archives, pp. 1-6; 2003; accessed at the following website: http://dc.engconfintl.org/heatexchanger/43).*
Mukherjee, R., "Effectively Design Shell-and-Tube Heat Exchangers," Chemical Engineering Progress, Feb. 1998, pp. 1-17.*
Master et al. (Engineering Conferences International Digital Archives, pp. 1-6; 2003; accessed at the following website: http://dc.engconfintl.org/heatexchanger/43) (of record).*
Shah, et al., Fundamentals of Heat Exchanger Design, Chapter 3: Basic Thermal Design Theory for Recuperators; pp. 97-231, John Wiley and Sons; Published online Nov. 6, 2007.*
Mukherjee, R., Chemical Engineering Progress, Feb. 1998, pp. 1-17 (of record).*
Mukherjee, R., "Effectively Design Shell-and-Tube Heat Exchangers," Chemical Engineering Progress, Feb. 1998, pp. 1-17 (of record).*

* cited by examiner

*Primary Examiner* — Soren Harward
*Assistant Examiner* — Paul D. Pyla
(74) *Attorney, Agent, or Firm* — Woodard, Emhardt, Moriarty, McNett & Henry, LLP

(57) ABSTRACT

Described are methods for pretreating lignocellulosic biomass that comprise thermally conditioning the biomass by flow processing an aqueous slurry of the biomass through an outer passage(s) of one or more heat exchange devices while circulating a heat exchange fluid through an inner passage(s) of the heat exchange device(s). Also described are methods for producing fermentation products, especially ethanol, from the pretreated biomass.

19 Claims, 5 Drawing Sheets

FLOW PROCESS FOR PRETREATMENT OF LIGNOCELLULOSIC BIOMASS

REFERENCE TO RELATED APPLICATIONS

This application is a National Stage of International Application No. PCT/US2009/048863, which is hereby incorporated by reference, which claims the benefit of U.S. Provisional Application No. 61/076,019 filed Jun. 26, 2008, which is hereby incorporated by reference.

BACKGROUND

The present invention relates generally to the utilization of lignocellulosic biomass, and in certain embodiments to systems and processes useful for thermally treating aqueous slurries of lignocellulosic biomass under flow conditions to render cellulose therein more susceptible to hydrolysis.

As further background, increasing emphasis has been placed in recent years upon finding ways to efficiently produce fuels from renewable, non-petroleum resources. In one field of interest, fuel ethanol has been produced by fermentation of biomass feedstocks derived from plants. Currently, fuel ethanol is commercially produced from feedstocks of cornstarch, sugar cane and sugar beets. These materials, however, find significant competing uses in the food industry, and their expanded use to make fuel ethanol is met with increased prices and disruption of other industries. Alternative fermentation feedstocks and viable technologies for their utilization are thus highly sought after.

Lignocellulosic biomass feedstocks are available in large quantities and are relatively inexpensive. Such feedstocks are available in the form of agricultural wastes such as corn stover, corn fiber, wheat straw, barley straw, oat straw, oat hulls, canola straw, soybean stover, grasses such as switch grass, miscanthus, cord grass, and reed canary grass, forestry wastes such as aspen wood and sawdust, and sugar processing residues such as bagasse and beet pulp. Cellulose from these feedstocks is converted to sugars, which are then fermented to produce the ethanol.

A difficulty in using lignocellulosic feedstocks is that the cellulose content of the biomass is caught up in a structure that inhibits the accessibility of the cellulose to agents that convert it to sugars. For this reason, research has focused upon methods for pretreating lignocellulosic biomass to enhance the susceptibility of the cellulose to conversion to sugars. Such pretreatment processes are designed to break the lignin seal protecting the cellulose and to disrupt the crystalline structure of the cellulose. A variety of pretreatment methodologies have been explored for this purpose; including physical processes such as size reduction, steam explosion, liquid hot water, irradiation, cryomilling, and freeze explosion; and chemical processes such as acid hydrolysis, buffered solvent pumping, alkali or alkali/$H_2O_2$ delignification, solvents, ammonia; and microbial or enzymatic methods.

Despite previous efforts relating to pretreatments for lignocellulosic biomass feedstocks and its ultimate use in the production of ethanol, needs remain for improved and alternative biomass pretreatment processes and follow-on production of ethanol. In certain of its aspects, the present invention is addressed to these needs.

SUMMARY

In one embodiment, provided is a method for processing lignocellulosic biomass. The method includes providing a heat exchanger including an inner passage received within an outer passage, with the inner passage in heat exchange relationship with the outer passage. An aqueous biomass slurry including said lignocellulosic biomass is passed through the outer passage, and a heat exchange fluid is passed through the inner passage, so as to exchange heat between the aqueous biomass slurry and the heat exchange fluid.

In another embodiment, provided is a method for pretreating lignocellulosic biomass to increase its susceptibility to enzymatic hydrolysis. The method includes providing a particulate lignocellulosic biomass and mixing the particulate lignocellulosic biomass with an aqueous medium to prepare an aqueous biomass slurry including the lignocellulosic biomass at a solids level of at least 50 grams per liter. A heat exchanger is provided, including an inner passage received within an outer passage, with the inner passage in heat exchange relationship with the outer passage. The aqueous biomass slurry is passed through the outer passage of the heat exchanger, and a heat exchange fluid is passed through the inner passage of the heat exchanger, so as to exchange heat between the aqueous biomass slurry and the heat exchange fluid.

Additional embodiments of the invention as well as features and advantages thereof will be apparent from the descriptions herein.

DETAILED DESCRIPTION

Figure 1:
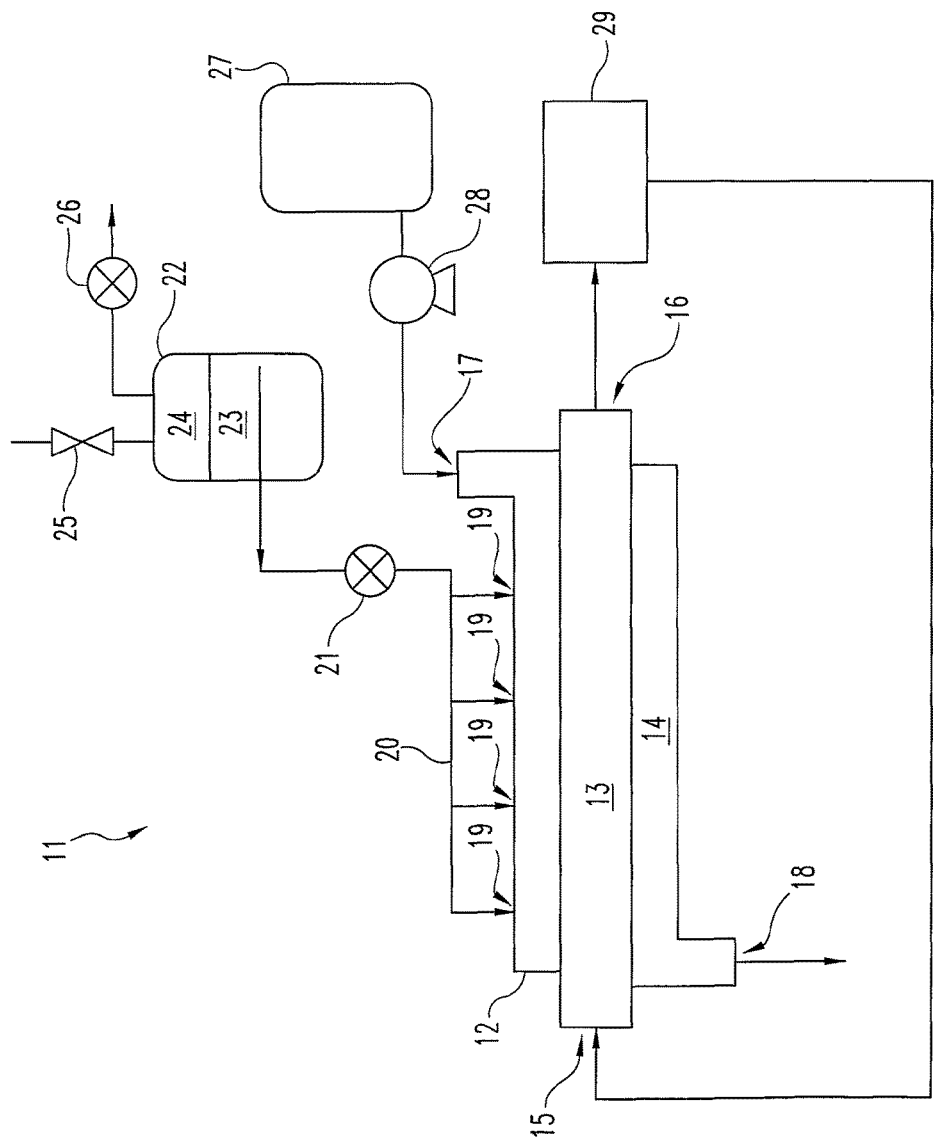
FIG. 1 is a schematic diagram of a heat exchange system useful for pretreatment of a lignocellulosic biomass slurry.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, certain aspects of the present invention relate to methods and systems for pretreating lignocellulosic biomass in an aqueous slurry. Additional aspects of the invention relate to processes utilizing pretreated biomass materials in the production of products, including fermentation products such as ethanol.

As used herein, the term "lignocellulosic biomass", is meant to refer to any type of biomass comprising lignin and cellulose such as, but not limited to, non-woody plant biomass, agricultural wastes and forestry residues and sugar-processing residues. For example, the cellulosic feedstock can include, but is not limited to, grasses, such as switch grass, cord grass, rye grass, miscanthus, mixed prairie grasses, or a combination thereof; sugar-processing residues such as, but not limited to, sugar cane bagasse and sugar beet pulp; agricultural wastes such as, but not limited to, soybean stover, corn fiber from grain processing, corn stover, oat straw, rice straw, rice hulls, barley straw, corn cobs, wheat straw, canola straw, oat hulls, and corn fiber; and forestry wastes, such as, but not limited to, recycled wood pulp fiber, sawdust, hardwood, softwood, or any combination thereof. Further, the lignocellulosic biomass may comprise lignocellulosic waste or forestry waste materials such as, but not limited to, paper sludge, newsprint, cardboard and the like. Lignocellulosic biomass may comprise one species of fiber or, alternatively, a lignocellulosic biomass feedstock may comprise a mixture of fibers that originate from different lignocellulosic materials.

Typically, the lignocellulosic material will comprise cellulose in an amount greater than about 2%, 5% or 10% and preferably greater than about 20% (w/w) to produce a significant amount of glucose. The lignocellulosic material can be of higher cellulose content, for example at least about 30% (w/w), 35% (w/w), 40% (w/w) or more. Therefore, the lignocellulosic material may comprise from about 2% to about 90% (w/w), or from about 20% to about 80% (w/w) cellulose, or from 25% to about 70% (w/w) cellulose, or about 35% to about 70% (w/w) cellulose, or more, or any amount therebetween.

Prior to pretreatment, the lignocellulosic biomass can be mechanically processed to increase its surface area. Such mechanical processing may include, for example, reducing the biomass to a particulate by grinding, milling, agitation, shredding, or other types of mechanical action.

In certain aspects, the lignocellulosic biomass will be used to create a pumpable slurry in combination with a suitable liquid, preferably an aqueous medium. The aqueous medium may be water alone, but in other embodiments can include additives to enhance the pretreatment process such as acids or bases to adjust or maintain the pH of the aqueous medium. Aspects of the present invention are also applicable to systems which employ dilute acid pretreatment processes. Suitable acids for these or other purposes herein include for example inorganic or organic acids, e.g. sulfuric, hydrochloric, phosphoric nitric, acetic, citric or formic acid. Suitable bases for these purposes include for example alkali or alkaline earth metal hydroxides, e.g. sodium or potassium hydroxide, or other hydroxide bases such as ammonium hydroxide. In certain preferred forms, the aqueous medium will be adjusted initially and/or during a thermal pretreatment process by the addition of acid or base to provide a pH that is near neutral, so as to avoid the occurrence of any significant acid- or base-catalyzed autohydrolysis of the lignocellulosic material, for example a pH in the range of about 5 to about 8. Additional information as to suitable conditions for pH-controlled lignocellulosic biomass pretreatments is found in U.S. Pat. No. 5,846,787, which is hereby incorporated herein by reference in its entirety. Other additives that may be present in the aqueous biomass slurry include, as illustrations, surfactants, e.g. vegetable oils such as soybean oil, canola oil, and others, to serve as intercalating agents.

The aqueous slurry of the lignocellulosic biomass will typically be relatively highly concentrated in solids. In certain embodiments, the aqueous slurry will be comprised at least about 10 grams per liter (g/l) of lignocellulosic biomass solids, preferably at least about 50 g/l, more preferably at least about 100 g/l, and typically in the range of about 100 g/l to about 300 g/l. It will be understood, however, that other solids concentrations may be used in broader aspects of the invention.

In aspects of the invention, the aqueous biomass slurry will be subjected to thermal heating and cooling cycles during pressurized flow through the inlets and outlets of a plurality of (two or more) heat exchangers. In such processing, the treatment system will be designed to facilitate maintaining the aqueous slurry under a pressure substantially at or above its saturation vapor pressure, so as to maintain the water and/or other liquid(s) of the slurry in liquid form as much as possible. However, at times, including during startup, passages within the system may encounter localized reductions in pressure due at least in part to the extended nature of the passages within the heat exchangers. This in turn may result in localized vaporization of water and/or other liquids which may cause undesired chemical changes in the biomass slurry and undesired phenomena in the system components. To address this problem, in certain embodiments, systems of the invention include one or more feed points at position(s) between the inlet and outlet of a heat exchanger passage, into which a pressurized liquid medium, suitably an aqueous medium, is fed into the heat exchanger passage carrying the aqueous biomass slurry. This feed of a pressurized liquid can serve to locally regulate the pressure in the passage and reduce the incidence of localized pressure drops in the system. Alternatively, a feed of pressurized gas, e.g. nitrogen or carbon dioxide gas, can be employed.

A wide variety of heat exchangers may be used in systems and methods of the present invention. These include, for example, simple tube-in-tube heat exchangers and core-and-shell heat exchangers. In accordance with embodiments of the invention, the aqueous biomass slurry flow will be provided in the outer passage or passages of the heat exchanger, for example, the annular outer passage in a simple tube-in-tube exchanger, or the shell of a core-and-shell heat exchanger, while the heat exchange fluid flow will be provided within the inner passage or passages. The flow of materials in the inner and outer passages can be co-current or counter-current in a given heat exchanger.

In systems including multiple heat exchangers, the aqueous biomass slurry flow will be provided in the outer passage of at least one heat exchanger of the system, in certain embodiments in two or more heat exchangers of the system, and in certain preferred embodiments in all heat exchangers of the system. Thus, in some embodiments having multiple heat exchangers, one or more heat exchangers of the system may include the aqueous biomass slurry flow in the inner passage(s) while the heat exchange fluid flow can occur in the outer passage(s). Combinations of flow patterns in multiple heat exchange devices of the system, e.g. connected in series, may be used. Further, in certain preferred aspects, in at least one heat exchanger of the system, and optionally multiple heat exchangers, to effect heat recovery, a first amount of aqueous biomass slurry at a relatively lower temperature is passed through the inner passage(s) while a second amount of aqueous biomass slurry at a relatively higher temperature is passed through the outer passage(s), so as to exchange heat between the first and second amounts of aqueous biomass slurry.

In all of the above-mentioned embodiments, the flow in the passages of the heat exchanger of the aqueous biomass slurry and the heat exchanger fluid may be reversed. The heat exchanger fluid can be fed into the inner passage of a heat exchanger while the aqueous biomass slurry is passed through the outer passage of the heat exchanger. In systems including multiple heat exchangers, the flow of the aqueous biomass may be through both the inner or outer passages of different exchangers in the system of heat exchangers, with the heat exchanger fluid passing through the passage not used by the aqueous biomass.

With reference now to FIG. 1, shown is one embodiment of a heat exchange system that is useful for pretreating a lignocellulosic biomass slurry. Heat exchange system 11 includes a core-and-shell heat exchanger 12 having a core portion 13 including one or more fluid passages and a shell portion 14 including one or more fluid passages and encompassing the core portion 13. Heat exchanger 12 includes a core inlet end 15 including one or more openings communicating with the passage or passages of core 13 and a core outlet end 16 including one or more outlet openings communicating with the passage or passages of core 13. The shell portion 14 of heat exchanger 12 includes a shell inlet end 17 having one or more openings communicating with the one or more passages in shell portion 14 and a shell outlet end 18 having one or more openings communicating with the one or more passages in shell portion 14. The volume of the shell portion of the heat exchanger is in general greater than the volume of the tube portion of the heat exchanger. Thus, the volume ratio of the shell portion of the heat exchanger to the core portion of the heat exchanger is at least about 3:1, or at least about 5:1, typically in the range of about 5:1 to about 50:1 and preferably in the range of about 10:1 to about 30:1.

In accordance with aspects of the present invention, heat exchanger 12 also includes one or more openings, and preferably a plurality of openings 19, positioned between the shell inlet end 17 the shell outlet end 18. A source of pressurized liquid, such as a pressurized aqueous medium, is fluidly coupled to the one or more openings 19. Opening(s) 19 are preferably relatively small, so as to minimize dilution of the aqueous slurry by the added pressurized liquid. Preferably, within a given heat exchanger, opening(s) 19 will be sized and numbered sufficiently small so as to result in a dilution of the aqueous slurry in that heat exchanger by no more than about 5% (w/w), more preferably no more than about 2% (w/w). For these purposes, in certain embodiments, the opening(s) 19 will have a cross-sectional area (considered together) of less than about 20% of the cross-sectional area of the shell (or outer) passage portion 14 of the heat exchanger, more preferably less than about 10%.

The source of pressurized liquid or gas can include a feed line or lines 20 connected via a valve 21 to a pressurized tank 22. Pressurized tank 22 can include an incompressible liquid 23 such as an aqueous medium, and a pressurized gaseous atmosphere 24 exerting pressure upon the liquid 23. Pressurized atmosphere 24 can, for example, comprise water vapor, air, nitrogen, or any suitable gas or combination of gases for providing a gaseous environment that exerts pressure on liquid 23. A pressure relief valve 25 can be provided on tank 22, as well as a bleed valve 26 for bleeding the system as necessary.

Heat exchange system 11 also includes a source 27 of an aqueous slurry of a lignocellulosic biomass material, and a pump 28 for pumping the aqueous slurry under pressure through the shell side of heat exchanger 12. System 11 includes a source 29 of a heat exchange fluid coupled to the core side of heat exchanger 12. Source 29 can provide the heat exchange fluid in gaseous or liquid form and at a temperature that is higher or lower than that of the aqueous biomass slurry. In certain embodiments disclosed herein, the source 29 provides the heat exchange fluid in the form of a liquid aqueous medium or steam. The heat exchange fluid from source 29 is circulated through the core portion 13 from core inlet end 15 to the core outlet end 16.

In use, the aqueous biomass slurry from source 27 can be circulated through the shell portion 14 of heat exchanger 12 at a pressure substantially at or exceeding its saturation vapor pressure in order to facilitate maintaining the water and/or other liquid of the slurry in liquid form. However, as the aqueous biomass slurry passes through the shell portion 14 of heat exchanger 12, localized pressure drops may develop which may lead to vaporization or flashing of water and/or other liquid from the aqueous slurry. This in turn interrupts the desired liquid-form modification of the lignocellulosic biomass and decreases the overall efficiency of the pretreatment process, and also may tend to cause "water hammer" or "bump" in the system which exerts unnecessary stresses on system components. To ameliorate the occurrence of localized pressure drops, and incompressible liquid medium such as an aqueous liquid medium, suitably water alone, is fed under pressure from tank 22 through the openings 19 at intermediate locations within heat exchanger 12. This intermediate feed will be conducted at a pressure sufficient to reduce the incidence of localized pressure drops, typically at a pressure at or above the initial feed pressure of the aqueous biomass slurry into the shell inlet end 17 of heat exchanger 12. Such localized pressure regulation with an incompressible liquid may be used at any desired time during processing of the aqueous biomass slurry through heat exchanger 12, and may be particularly beneficial when used during start-up operations.

It will be understood that the source of pressurized liquid for intermediate feed to heat exchanger 12 can vary from that shown in FIG. 1 in other embodiments. For example, pressurized liquid can be provided by a pump or any other suitable mechanism. Further, in accordance with additional aspects of the invention, the pressured liquid for intermediate feed to the heat exchanger can contain additives for modifying the aqueous biomass slurry as it passes through the heat exchanger system. Such additives can include, for example, any of those discussed herein, including acid or base for adjusting pH, surfactants, e.g. vegetable oils such as soybean oil, canola oil, and others, to serve as intercalating agents. In certain embodiments, such additives can be added to the pressurized liquid feed at selected times under control of appropriate valving and supply systems. Other embodiments, such additives can be included as a standard measure in the pressurized liquid feed. In these embodiments, additional control and variation of the pretreatment conditions for the lignocellulosic biomass can be provided during the process.

Figure 2:
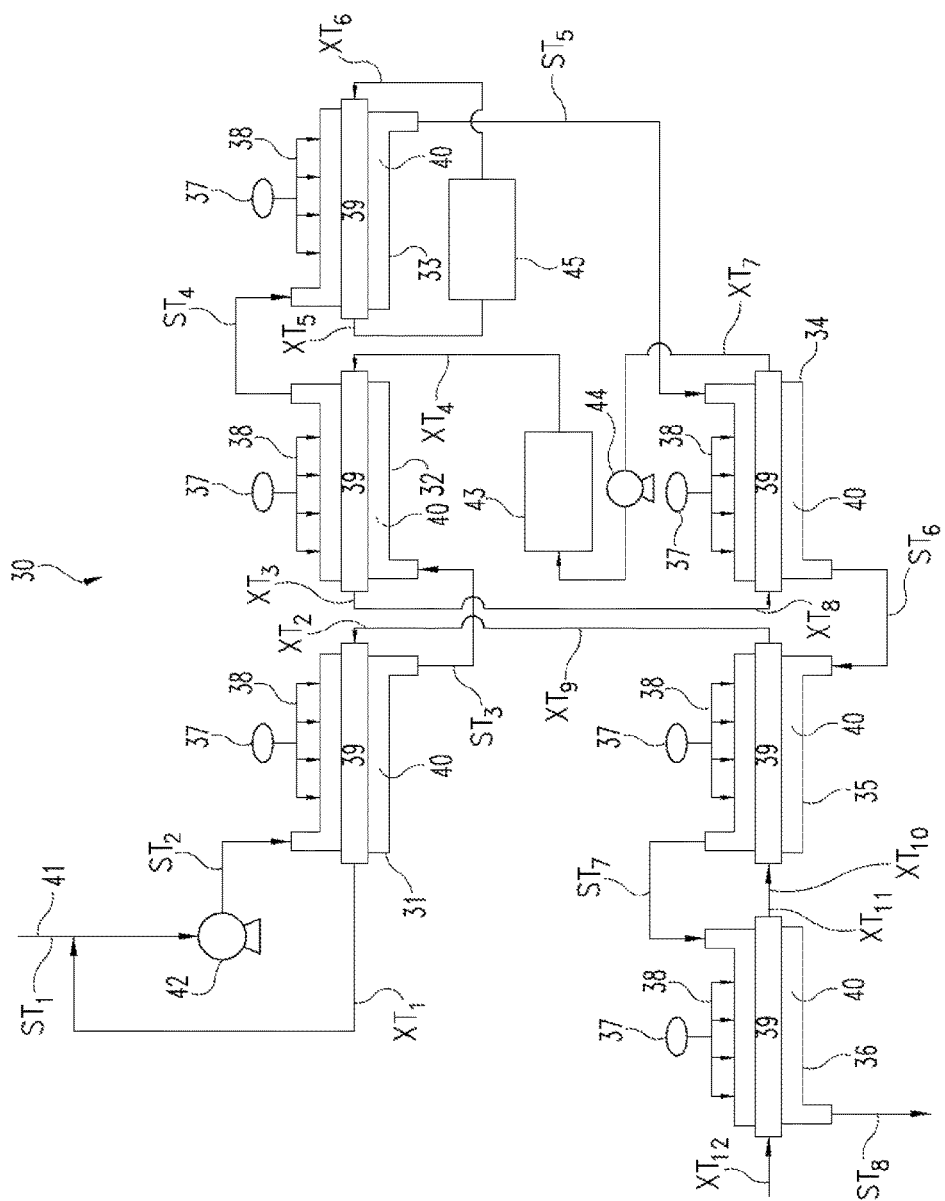
FIG. 2 is a schematic diagram of a lignocellulosic biomass pretreatment system with a plurality of heat exchangers.

With reference now to FIG. 2, shown is a lignocellulosic biomass pretreatment system 30 that includes a plurality of heat exchangers. In system 30, an aqueous slurry of a lignocellulosic biomass is passed through the shell sides of the heat exchangers and a heat exchange fluid is passed through the core sides of the heat exchangers. In particular, system 30 includes heat exchanger 31, heat exchanger 32, heat exchanger 33, heat exchanger 34, heat exchanger 35, and heat exchanger 36, having their shell sides coupled in series. As examples, core and shell or simple tube-in-tube heat exchangers may be used. In the illustrated embodiment, each heat exchanger is fluidly coupled to a source 37 of pressurized liquid through feed lines 38 that open into a corresponding plurality of openings in the shell sides 40 of the heat exchangers. The heat exchangers also include a core side 39 encompassed by the shell side 40. This source of pressurized incompressible liquid can be such as that described in the proceeding passages and can be useful to locally regulate pressures within the system 30.

System 30 includes a source of lignocellulosic biomass 41 and pump 42 for pumping the biomass in slurry form through the system 30. As illustrated, the biomass slurry is pumped through the shell sides 40 of the heat exchangers of system 30, whereas various heat exchange fluids (in some cases potentially including another amount of aqueous biomass slurry or a fraction thereof) are passed through the cores 39 of the heat exchangers. As will be discussed further below, in one module of the heat exchange fluid side, a source of heated, liquid-form water 43 is pumped by pump 44 through the cores 39 of heat exchangers 32 and 34 of system 30. In another module of the heat exchange fluid side of system 30, a source of steam 45, such as a boiler, is provided to circulate steam through the core 39 of heat exchanger 33.

Generally in system 30, as the aqueous biomass slurry is pumped through heat exchangers 31, 32, and 33, it is subjected to increasing temperatures. For example, the temperature $ST_1$ of the initial dry lignocellulosic biomass can be room temperature, for example about 20° C. to about 25° C. After being combined with heated liquids such as a heated aqueous medium, the temperature $ST_2$ of the aqueous biomass slurry can be about 50° C. to about 90° C. The temperature $ST_3$ of the aqueous biomass slurry after exiting the first heat exchanger 31 will be higher than $ST_2$, typically in the range of about 70° C. to about 120° C. The temperature $ST_4$ of the aqueous slurry after exiting heat exchanger 32 can typically be about 120° C. to about 170° C. The temperature $ST_5$ of the aqueous biomass slurry after exiting heat exchanger 33 can typically be in the range of about 150° C. to about 220° C. From this point, the aqueous biomass slurry is passed through a series of heat exchangers which decrease its temperature. Thus, the temperature $ST_6$ of the aqueous slurry as it exits heat exchanger 34 can be in the range of about 100° C. to about 150° C., the temperature $ST_7$ of the aqueous slurry after exiting heat exchanger 35 can be about 50° C. to about 100° C., and the temperature $ST_8$ after exiting heat exchanger 36 can typically be about 30° C. to about 70° C.

On the heat exchange fluid side of the system, the temperature $XT_1$ of the heat exchange fluid exiting heat exchanger 31 can typically range from about 70° C. to about 100° C., where as the temperature $XT_2$ of the heat exchange fluid entering heat exchanger 31 can typically be in the range of about 90° C. to about 120° C. The temperature $XT_3$ of the heat exchange fluid exiting heat exchanger 32 can typically be in the range of about 100° C. to about 150° C., whereas the temperature $XT_4$ of the heat exchange fluid entering heat exchanger 32 can typically be about 130° C. to about 180° C. The temperature $XT_5$ of the heat exchange fluid exiting heat exchanger 33 can typically be in the range of about 140° C. to about 180° C., whereas the temperature $XT_6$ of the heat exchange fluid entering heat exchanger 33 can typically in the range of about 150° C. to about 230° C. The temperature $XT_7$ of the heat exchange fluid exiting heat exchanger 34 can typically be about 130° C. to about 180° C., while the temperature $XT_8$ of the heat exchange fluid entering heat exchanger 34 can typically be about 100° C. to about 150° C. The temperature $XT_9$ of the heat exchange fluid exiting heat exchanger 35 can typically be in the range of about 90° C. to about 120° C., where as the temperature $XT_{10}$ of the heat exchange fluid entering heat exchanger 35 can typically be about 60° C. to about 110° C. The temperature $XT_{11}$ of the heat exchange fluid exiting heat exchanger 36 can typically be about 60° C. to about 110° C. The temperature $XT_{12}$ of the heat exchange fluid entering heat exchanger 36 can typically be in the range of about 20° C. to about 70° C.

In certain processes of the invention, the lignocellulosic biomass utilized will be corn stover or corn fiber (derived from the hulls of corn kernels). In preferred such processes, the temperatures given in Table 1 below are applied in a system such as that described in connection with FIG. 2:

TABLE 1

| Corn Fiber | | | | Corn Stover | | | |
|---|---|---|---|---|---|---|---|
| ST Temperature (±10° C.) | | XT Temperature (±10° C.) | | ST Temperature (±10° C.) | | XT Temperature (±10° C.) | |
| $ST^1$ | 20° C. | $XT^1$ | 80° C. | $ST^1$ | 20° C. | $XT^1$ | 100° C. |
| $ST^2$ | 70° C. | $XT^2$ | 105° C. | $ST^2$ | 90° C. | $XT^2$ | 135° C. |
| $ST^3$ | 95° C. | $XT^3$ | 105° C. | $ST^3$ | 125° C. | $XT^3$ | 135° C. |
| $ST^4$ | 140° C. | $XT^4$ | 150° C. | $ST^4$ | 170° C. | $XT^4$ | 180° C. |
| $ST^5$ | 160° C. | $XT^5$ | 160° C. | $ST^5$ | 190° C. | $XT^5$ | 190° C. |
| $ST^6$ | 115° C. | $XT^6$ | 170° C. | $ST^6$ | 145° C. | $XT^6$ | 200° C. |
| $ST^7$ | 80° C. | $XT^7$ | 150° C. | $ST^7$ | 110° C. | $XT^7$ | 180° C. |
| $ST^8$ | 50° C. | $XT^8$ | 105° C. | $ST^8$ | 80° C. | $XT^8$ | 135° C. |
| | | $XT^9$ | 105° C. | | | $XT^9$ | 135° C. |
| | | $XT^{10}$ | 70° C. | | | $XT^{10}$ | 100° C. |
| | | $XT^{11}$ | 70° C. | | | $XT^{11}$ | 100° C. |
| | | $XT^{12}$ | 50° C. | | | $XT^{12}$ | 80° C. |

It will be understood that the temperature ranges given herein for the biomass slurry (ST) and heat exchange fluids (XT) at various points in the system can vary in accordance with the particular process at hand. Appropriate temperatures for a given process will depend upon system requirements, pretreatment requirements, the particular lignocellulosic biomass undergoing pretreatment, and other factors. It will also be understood that while those temperature ranges given above illustrate certain embodiments of the invention, other embodiments with other temperature ranges are also encompassed by broader aspects of the invention. As well, the number of heat exchangers and stages of heating and cooling in the system can vary from those disclosed in system 30 without departing from the spirit and scope of broader aspects of the present invention.

The aqueous lignocellulosic biomass can be passed through the heat exchanger(s) of the system at any suitable flow rate. Flow rates of about 5 gallons (US) per minute (gal/min) to about 200 gal/min will be typical, with flow rates of about 40 gal/min to about 100 gal/min being more preferred. In addition, in portions of the pretreatment system (e.g. in some or all heat exchangers) in which the biomass slurry is processed at pressures above the saturation vapor pressure of water or other liquid, the pressure will typically be in the range of about 50 to about 500 pounds per square inch (psi).

The aqueous lignocellulosic biomass is pretreated by a heating and cooling cycle, but it is desirable to control the heat history of the lignocellulosic biomass in these systems. Overly extended heating can cause degradation of the lignocellulosic biomass, which can result in chemical degradation products that can inhibit the enzymatic processes used for the production of useful products from the lignocellulosic biomass. In accordance with embodiments of the invention, the lignocellulosic biomass can be passed through the shell portion of the heat exchanger to provide relatively rapid and effective heating and cooling rates to achieve pretreatment of the lignocellulosic biomass, without causing significant undesired chemical degradation of the lignocellulosic biomass, even utilizing relatively high shell volume (biomass side) to core volume (heat transfer fluid side) ratios, for example such ratios of at least about 3:1, or at least about 5:1, typically in the range of about 5:1 to about 50:1, and more preferably about 10:1 to about 30:1.

Other preferred aspects of the system 30 are illustrated in FIG. 2. For example, countercurrent heat recovery can be incorporated into the system. In particular, a single heat exchange fluid can be circulated through heat exchangers 35 and 36 during which the heat exchange fluid picks up heat from the aqueous biomass slurry during its cooling phase, and that same fluid can then be circulated through heat exchanger 31 to transfer heat to the aqueous slurry during its heating phase. Also, hot water from liquid water source 43 can be circulated through heat exchanger 32 during which it transfers heat to the aqueous biomass slurry during its heating phase, and then through heat exchanger 34 during which the liquid water picks up heat from the aqueous slurry during its cooling phase. These and other arrangements of the heating and cooling stages of the system 30 will be apparent to those skilled in the art from the descriptions herein, and can be used in embodiments of the invention. Further, it will be understood that pretreatment processes as described herein can be used in combination with other pretreatment processes designed to increase the susceptibility of the biomass to enzymatic hydrolysis, including for example chemical, mechanical and/or microbiological pretreatment processes.

Figure 3:
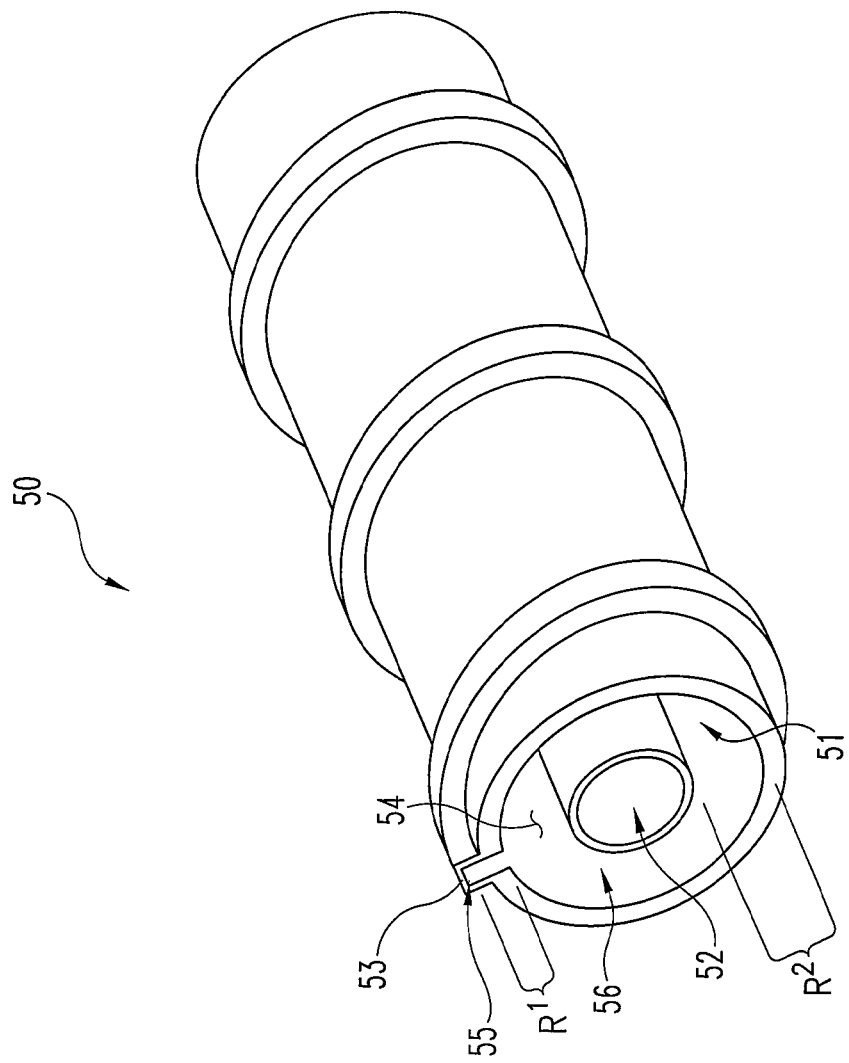
FIG. 3 provides a perspective view of a heat exchange tube arrangement of the invention with a helical groove in an outer passage.

In additional embodiments of the invention, a heat exchanger useful for pretreating a biomass slurry defines at least one helical groove along at least a portion of its length, and potentially the entire length of an outer flow passage of the heat exchanger. With reference to FIG. 3, shown is a perspective view of a tube-in-tube arrangement of one embodiment of such a heat exchanger. The arrangement for heat exchanger 50 thus includes at least one outer passage 51, at least one inner passage 52, and a helical groove 53 defined along an outer wall 54 of outer passage 51. Helical groove 53 can, for example, provide a secondary, helical passage 55 having a radial dimension $R^1$ that is at least about 10% of that of the radial dimension $R^2$ of the primary outer passage 56, with radial dimension $R^1$ typically being in the range of about 10% to about 50% of that of radial dimension $R^2$, more typically in the range of about 10% to about 20%. Helical groove 53 can serve to enhance mixing of the aqueous biomass slurry as it passes through the overall outer passage 51 including primary passage 56 and helical passage 55, so as to help to prevent plugging of outer passage 51. It will be understood that helical groove 53 can be used instead of or in addition to fins, baffles, or other turbulence-inducing members located in outer passage 51. Heat exchanger(s) 50 can be used in overall systems containing a plurality of heat exchangers, e.g. a system 30 as disclosed in FIG. 2, and in so doing can be used for one, two or more, or all heat exchangers of the system.

In accordance with other aspects of the invention, lignocellulosic biomass that has been pretreated as described herein can be utilized to produce useful products, such as ethanol. In the production of ethanol, the pretreated biomass can be subjected to enzymatic hydrolysis with a cellulase enzyme. In this regard, a cellulase enzyme is an enzyme that catalyzes the hydrolysis of cellulose to products such as glucose, cellobiose, and/or other cellooligosaccharides. Cellulase enzymes may be provided as a multienzyme mixture comprising exo-cellobiohydrolases (CBH), endoglucanases (EG) and beta-glucosidases (betaG) that can be produced by a number of plants and microorganisms. The process of the present invention can be carried out with any type of cellulase enzymes, regardless of their source; however, microbial cellulases provide preferred embodiments. Cellulase enzymes can, for example, be obtained from fungi of the genera *Aspergillus, Humicola*, and *Trichoderma*, and from the bacteria of the genera *Bacillus* and *Thermobifida*.

Following enzymatic hydrolysis of the pretreated biomass, an aqueous medium containing the resulting sugars can be subjected to fermentation to produce ethanol. In certain modes of practice, unhydrolyzed solids, typically including lignin, can be separated from liquids as a byproduct, for example by centrifugation or in a settling tank. The unhydrolyzed solids can be sold into commercial channels such as feed industries or combusted to generate thermal energy to be provided to systems and methods of the invention.

The fermentation of the sugars to produce ethanol can be conducted with any of a wide variety of fermentive microorganisms such as yeast or bacteria, including genetically modified versions thereof, and using known techniques. The ethanol can then be purified from the fermented medium, for example by distillation.

EXAMPLE 1

Heat up profiles were obtained for aqueous lignocellulosic biomass in a tube and shell heat exchanger. The aqueous lignocellulosic biomass was prepared by mixing corn dry mill byproduct (lignocellulosic biomass) with water to make a slurry, which contained 22.8% solids (corn dry mill byproduct wt/total wt).

Figure 4:
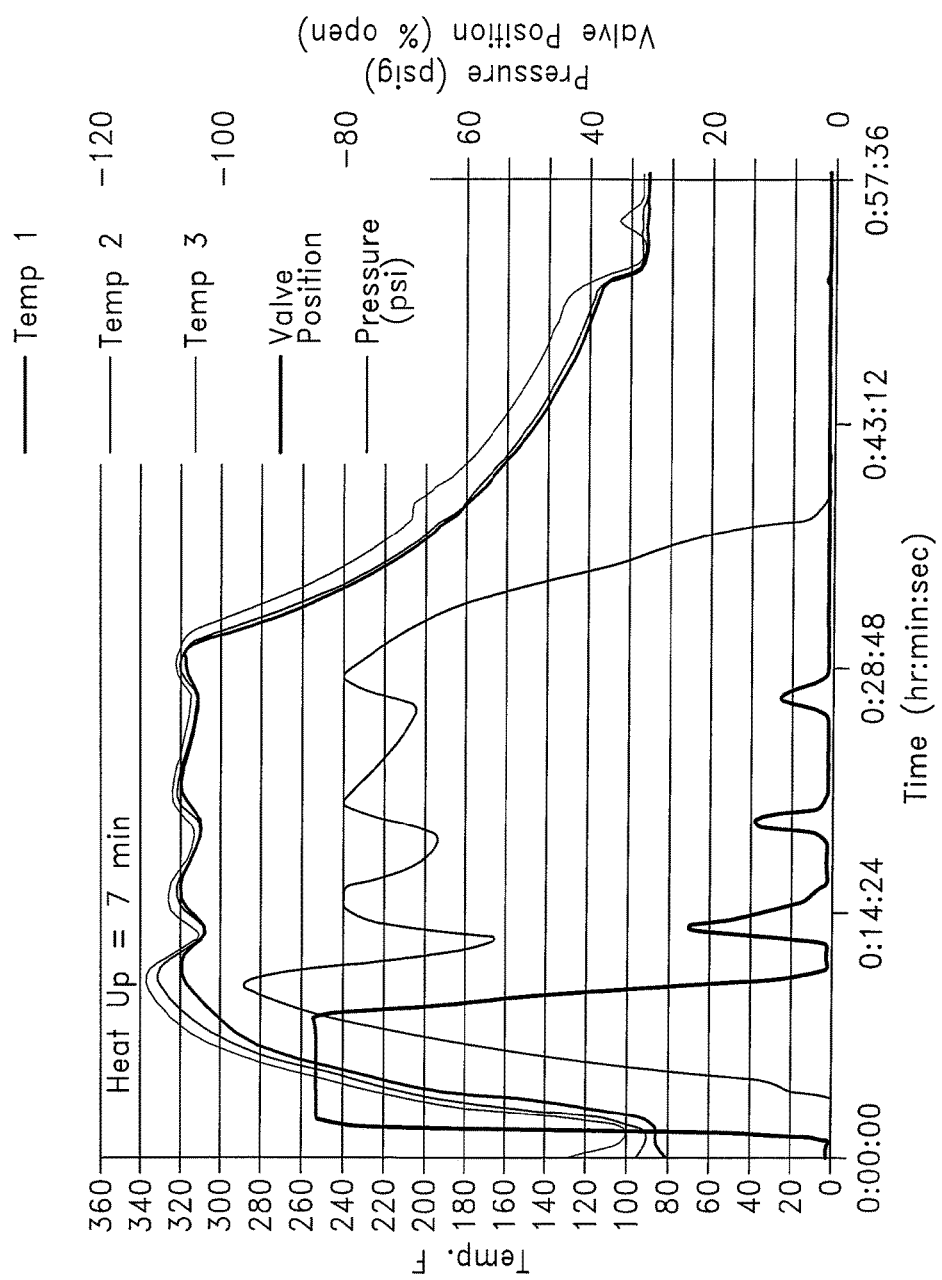
FIG. 4 shows the heat up profile for heating a slurry of biomass in the shell of a shell and tube heat exchanger.

For determining heat up rates for the aqueous lignocellulosic biomass in the shell portion of the heat exchanger, the aqueous lignocellulosic biomass (7.67 gallons of the 22.8% solids slurry of corn dry mill byproduct in water) was placed in the shell portion of a heat exchanger (100% filled shell portion). The heat exchanger was made with a 4" shell of schedule 40 pipe which was 155.75" in length, with a 1" schedule 80 pipe running along the central axis to supply heat with a heat transfer area of 2190 sq. in. Steam (200 psig) was passed through the central tube of the heat exchanger to heat the lignocellulosic biomass in the shell portion of the heat exchanger. The heat up profile is shown in FIG. 4, displaying a heat up time of 7 minutes for the lignocellulosic biomass going from room temperature to 160° C.

Figure 5:
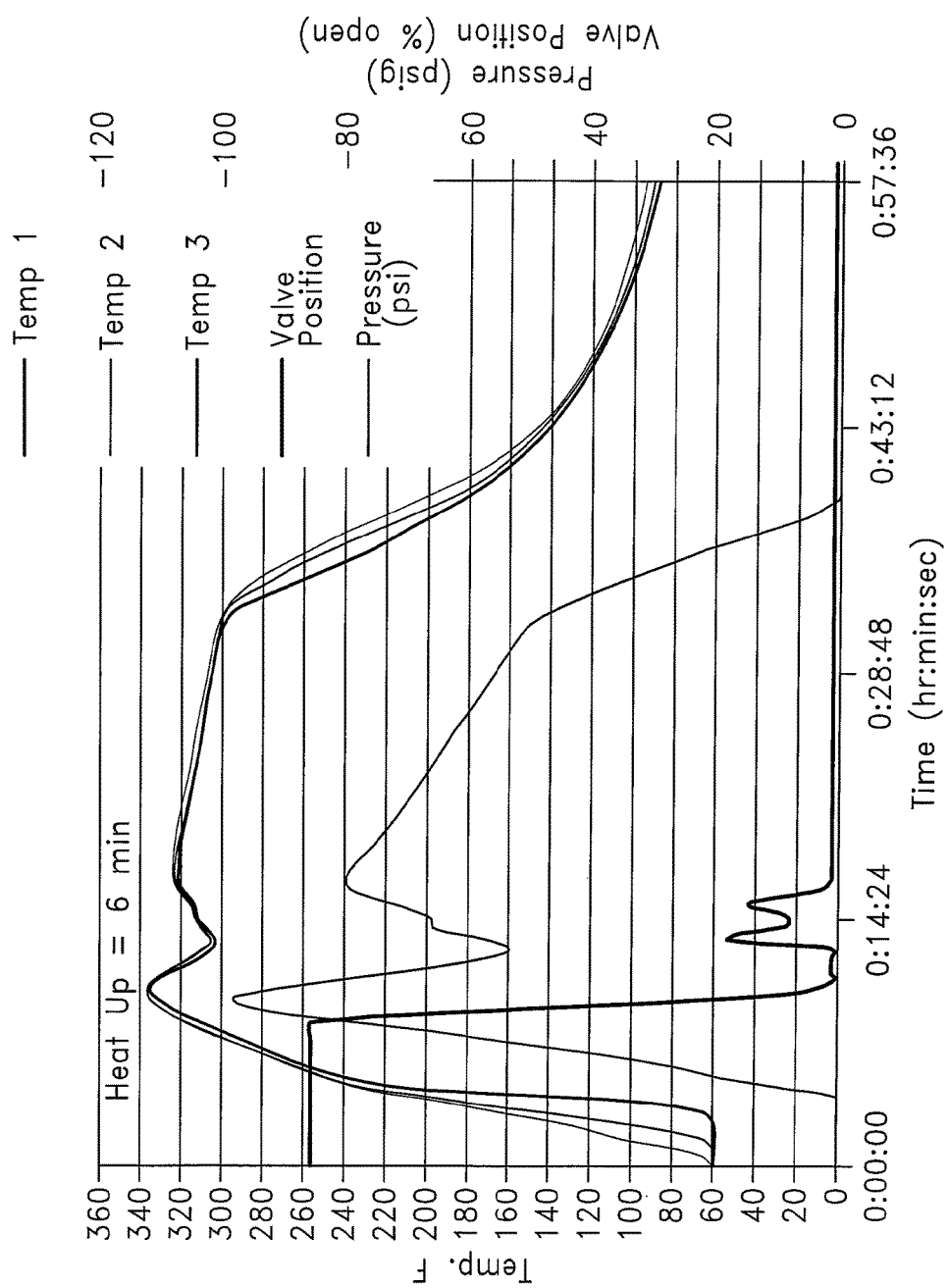
FIG. 5 shows the heat up profile for heating a slurry of biomass in the tube of a shell and tube heat exchanger.

For determining heat up rates for the aqueous lignocellulosic biomass in the tube portion of a heat exchanger, the aqueous lignocellulosic biomass (4.98 gallons of the 22.8% solids slurry of corn dry mill byproduct in water) was placed in the tube portion of a heat exchanger (100% filled). The heat exchanger was made with of an 8" shell of schedule 40 pipe which was 143.75" in length, with a 3" schedule 40 pipe running along the central axis to supply heat, with a heat transfer area of 3000 sq. in. Steam (200 psig) was passed through the shell portion of the heat exchanger to heat the lignocellulosic biomass in the tube portion of the heat exchanger. The heat up profile is shown in FIG. 5, displaying a heat up time of 6 minutes for the lignocellulosic biomass going from room temperature to 160° C.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for processing lignocellulosic biomass, comprising:
   providing lignocellulosic biomass;
   providing a first heat exchanger including a first heat exchanger inner passage received within a first heat exchanger outer passage, with the first heat exchanger inner passage in heat exchange relationship with the first heat exchanger outer passage, and wherein the first heat exchanger outer passage has a volume that is greater than that of the first heat exchanger inner passage, and wherein the first heat exchanger outer passage has an inlet and an outlet;
   first passing an aqueous biomass slurry including said lignocellulosic biomass at a solids level of at least 100 grams per liter through the first heat exchanger outer passage from the inlet of the first heat exchanger outer passage to the outlet of the first heat exchanger outer passage while passing a heat exchange fluid through the first heat exchanger inner passage so as to heat the aqueous biomass slurry, wherein said first passing heats the aqueous biomass slurry to a first temperature in the range of 70° C. to 120° C.;
   providing a second heat exchanger including a second heat exchanger inner passage received within a second heat exchanger outer passage, with the second heat exchanger inner passage in heat exchange relationship with the second heat exchanger outer passage, wherein the second heat exchanger outer passage has a volume that is greater than that of the second heat exchanger inner passage, and wherein the second heat exchanger outer passage has an inlet and an outlet, with the inlet of the second heat exchanger outer passage connected in series to the outlet of the first heat exchanger outer passage;
   after said first passing, second passing the aqueous biomass slurry through the second heat exchanger outer passage from the inlet of the second heat exchanger outer passage to the outlet of said second heat exchanger outer passage while passing a heat exchange fluid through the second heat exchanger inner passage, wherein during said second passing the aqueous biomass slurry, the biomass slurry is at a second temperature exceeding 100° C. and under a pressure substantially equal to or exceeding the saturation vapor pressure of water at said temperature;
   during said second passing, exchanging heat between the aqueous biomass slurry in the second heat exchanger outer passage and the heat exchange fluid in the second heat exchanger inner passage to cause heating of the aqueous biomass slurry to the second temperature and for a duration within the second heat exchanger outer passage to increase susceptibility of the lignocellulosic biomass to hydrolysis by a cellulase enzyme;
   during said second passing, feeding a liquid aqueous medium into the second heat exchanger outer passage through a plurality of openings at longitudinally spaced positions between the inlet and the outlet of the second heat exchanger outer passage so as to locally regulate pressure within the second heat exchanger outer passage and reduce incidence of localized pressure drops and water hammer in the second heat exchanger that would otherwise occur under conditions of said second passing step; and
   maintaining the aqueous biomass slurry under a pressure substantially equal to or exceeding the saturation vapor pressure of the aqueous biomass slurry during a pressurized flow of the aqueous biomass slurry from the inlet of the first heat exchanger outer passage to the outlet of the second heat exchanger outer passage.

2. The method of claim 1, wherein said aqueous biomass slurry includes the lignocellulosic biomass at a solids level of about 100 grams per liter to 300 grams per liter.

3. The method of claim 1, wherein the second heat exchanger comprises a shell portion providing said second heat exchanger outer passage and a core portion providing said second heat exchanger inner passage.

4. The method of claim 1, wherein said second heat exchanger is a tube-in-tube heat exchanger, with a single inner tube providing said second heat exchanger inner passage and a single outer tube providing said second heat exchanger outer passage.

5. The method of claim 3, wherein said second heat exchanger has a volume ratio of said shell portion to said core portion of at least about 3:1.

6. The method of claim 5, wherein said second heat exchanger has a volume ratio of said shell portion to said core portion of about 10:1 to about 30:1.

7. The method of claim 1, wherein said second heat exchanger outer passage has a volume at least three times that of said inner passage.

8. The method of claim 1, wherein said second passing the aqueous biomass slurry is conducted at a flow rate of about 5 gallons (US)/min to about 200 gallons(US)/min, and wherein said second heat exchanger has a helical groove defined along an outer wall of the second heat exchanger outer passage and sized and configured to enhance mixing of the aqueous biomass slurry as it passes through the second heat exchanger outer passage.

9. The method of claim 1, wherein said lignocellulosic biomass comprises corn fiber or corn stover.

10. The method of claim 1, wherein said second temperature exceeds about 150° C.

11. A method for pretreating lignocellulosic biomass to increase its susceptibility to enzymatic hydrolysis, comprising:
   providing particulate lignocellulosic biomass;
   mixing the particulate lignocellulosic biomass with an aqueous medium to prepare an aqueous biomass slurry including the lignocellulosic biomass at a lignocellulosic biomass solids level of at least 100 grams per liter;
   providing a plurality of heat exchangers each including an inner passage received within an outer passage, with said inner passage in heat exchange relationship with said outer passage, and with the outer passage having a volume greater than that of the inner passage;

first passing the aqueous biomass slurry through the outer passage of a first heat exchanger of said plurality of heat exchangers while passing a heat exchange fluid through the inner passage of the first heat exchanger so as to heat the aqueous biomass slurry, wherein said first passing heats the aqueous biomass slurry to a first temperature in the range of 70° C. to 120° C.;

after said first passing, second passing the aqueous biomass slurry through the outer passage of a second heat exchanger of said plurality of heat exchangers from an inlet to an outlet of the outer passage of the second heat exchanger while passing a heat exchange fluid through the inner passage of the second heat exchanger, wherein during said second passing the biomass slurry is heated to a second temperature greater than said first temperature, wherein the aqueous biomass slurry is maintained under a pressure substantially equal to or exceeding the saturation vapor pressure of water at said second temperature, and wherein during said second passing the lignocellulosic biomass is modified to increase susceptibility to hydrolysis by a cellulase enzyme;

during said second passing, feeding a liquid aqueous medium into the outer passage of the second heat exchanger through a plurality of openings at longitudinally spaced positions between the inlet and the outlet of the outer passage of the second heat exchanger so as to locally regulate pressure within the outer passage of the second heat exchanger and reduce incidence of localized pressure drops and water hammer in the second heat exchanger that would otherwise occur under conditions of said second passing step; and after said first passing and said second passing, third passing the aqueous biomass slurry through the outer passage of a third heat exchanger of said plurality of heat exchangers while passing a heat exchange fluid through the inner passage of the third heat exchanger, wherein during said third passing the aqueous biomass slurry is cooled; and maintaining the aqueous biomass slurry under a pressure substantially equal to or exceeding the saturation vapor pressure of the aqueous biomass slurry during a pressurized flow of the aqueous biomass slurry through a flow path including the outer passage of the first heat exchanger, the outer passage of the second heat exchanger and the outer passage of the third heat exchanger.

12. The method of claim 11, wherein said first passing and second passing the aqueous biomass slurry are conducted at a flow rate of about 5 gallons(US)/min to about 200 gallons (US)/min.

13. The method of claim 11, wherein at commencement of said first passing, the aqueous biomass slurry has a temperature in the range of about 50° C. to about 90° C.

14. The method of claim 11, wherein said second temperature exceeds about 150° C.

15. The method of claim 11, wherein said aqueous biomass slurry includes the lignocellulosic biomass at a solids level in the range of about 100 grams per liter to about 300 grams per liter.

16. The method of claim 11, wherein said heat exchanger has a volume ratio of said shell portion to said core portion of at least about 3:1.

17. A method for processing lignocellulosic biomass, comprising:

providing particulate lignocellulosic biomass;

providing a first heat exchanger, a second heat exchanger and a third heat exchanger each including an inner passage received within an outer passage, with said inner passage in heat exchange relationship with said outer passage, and with the outer passage having a volume that is greater than that of the inner passage;

first passing an aqueous biomass slurry including said lignocellulosic biomass at a lignocellulosic biomass solids level of at least 100 grams per liter through said outer passage of said first heat exchanger while passing a heat exchange fluid through said inner passage of said first heat exchanger so as to heat the aqueous biomass slurry, wherein said first passing heats the aqueous biomass slurry to a first temperature in the range of 70° C. to 120° C.;

after said first passing, second passing the aqueous biomass slurry through said outer passage of said second heat exchanger from an inlet to an outlet of said outer passage of said second heat exchanger while passing a heat exchange fluid through said inner passage of said second heat exchanger so as to heat the aqueous biomass slurry, wherein during said second passing the aqueous biomass slurry is heated to a second temperature exceeding the first temperature, and is maintained under a pressure substantially equal to or exceeding the saturation vapor pressure of water at said second temperature;

during said second passing, feeding a liquid aqueous medium into said outer passage of said second heat exchanger through a plurality of openings at longitudinally spaced positions between said inlet and said outlet of said outer passage of said second heat exchanger so as to locally regulate pressure within said outer passage of said second heat exchanger and reduce incidence of localized pressure drops and water hammer in said second heat exchanger that would otherwise occur under conditions of said second passing step;

after said first passing and said second passing, third passing the aqueous biomass slurry through said outer passage of said third heat exchanger while passing a heat exchange fluid through said inner passage of said third heat exchanger, wherein during said third passing the aqueous biomass slurry is cooled;

maintaining the aqueous biomass slurry under a pressure substantially equal to or exceeding the saturation vapor pressure of the aqueous biomass slurry during a pressurized flow of the aqueous biomass slurry through a flow path including said outer passage of said first heat exchanger, said outer passage of said second heat exchanger and said outer passage of said third heat exchanger; and wherein during said first passing, said second passing, and said third passing, said aqueous biomass slurry is maintained at a pH in the range of about 5 to about 8.

18. The method of claim 17, wherein the first heat exchanger is a core and shell heat exchanger with the core having a plurality of core passages providing said inner passage.

19. The method of claim 17, wherein the aqueous biomass slurry includes the lignocellulosic biomass at a solids level of 100 grams per liter to about 300 grams per liter, and wherein said second temperature exceeds 150° C.

* * * * *